(12) United States Patent
Fechner et al.

(10) Patent No.: US 9,173,822 B2
(45) Date of Patent: Nov. 3, 2015

(54) USE OF GLASS COMPOSITIONS FOR ACHIEVING AN ANTIOXIDATIVE EFFECT

(75) Inventors: Joerg Hinrich Fechner, Mainz (DE); Jose Zimmer, Ingelheim (DE); Sean Lee, Karlsruhe (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 10/889,212

(22) Filed: Jul. 13, 2004

(65) Prior Publication Data

US 2005/0013873 A1      Jan. 20, 2005

(30) Foreign Application Priority Data

Jul. 14, 2003   (DE) .................................. 103 32 011

(51) Int. Cl.
| | |
|---|---|
| A61K 33/38 | (2006.01) |
| A61K 33/42 | (2006.01) |
| C03C 3/16 | (2006.01) |
| C03C 3/076 | (2006.01) |
| A61K 8/25 | (2006.01) |
| A61Q 11/00 | (2006.01) |
| A61Q 15/00 | (2006.01) |
| A61Q 19/08 | (2006.01) |
| C03C 3/00 | (2006.01) |
| C03C 4/00 | (2006.01) |

(52) U.S. Cl.
CPC . *A61K 8/25* (2013.01); *A61Q 11/00* (2013.01); *A61Q 15/00* (2013.01); *A61Q 19/08* (2013.01); *C03C 3/00* (2013.01); *C03C 4/00* (2013.01); *C03C 4/0007* (2013.01); A61K 2800/522 (2013.01)

(58) Field of Classification Search
CPC .......... A61K 33/38; A61K 33/42; C03C 3/16; C03C 3/076
USPC ........ 424/67, 70.9, 70.12, 76.9, 78.03, 78.05, 424/78.07, 401, 409, 439, 484, 601, 602, 424/641, 646, 660, 724, 722
See application file for complete search history.

(56) References Cited

U.S. PATENT DOCUMENTS

| | | | | |
|---|---|---|---|---|
| 4,428,774 | A * | 1/1984 | Drake et al. ............... | 106/14.39 |
| 5,019,293 | A | 5/1991 | Burlitch | |
| 5,196,381 | A * | 3/1993 | Hu et al. ........................ | 501/10 |
| 5,296,026 | A * | 3/1994 | Monroe et al. .................. | 106/35 |
| 5,614,006 | A * | 3/1997 | Algar ........................ | 106/18.31 |
| 5,880,094 | A * | 3/1999 | Tam ................................. | 514/12 |
| 6,475,631 | B1 * | 11/2002 | Yamamoto et al. ........... | 428/480 |
| 6,482,444 | B1 * | 11/2002 | Bellantone et al. ........... | 424/618 |
| 2002/0086039 | A1 * | 7/2002 | Lee et al. ....................... | 424/401 |
| 2003/0008759 | A1 | 1/2003 | Martin et al. | |

FOREIGN PATENT DOCUMENTS

| | | | |
|---|---|---|---|
| DE | 101 41 230 | 3/2003 | |
| DE | 10213630 | 3/2003 | |
| EP | 0 003 903 B1 | 12/1982 | |
| EP | 1364639 A2 * | 11/2003 | ............... A61K 7/00 |
| JP | 54-160576 A | 12/1979 | |
| JP | 58-133320 A | 8/1983 | |
| JP | 09-291325 A | 11/1997 | |
| JP | 2001-291770 A | 10/2001 | |
| WO | WO 01/03650 | 1/2001 | |
| WO | WO 01/72262 | 10/2001 | |
| WO | WO 03/050052 | 6/2003 | |
| WO | WO 03/050053 | 6/2003 | |
| WO | WO 03059834 | 7/2003 | |

OTHER PUBLICATIONS

Burdock (Encyclopedia of food and color additives 1997, vol. 3, pp. 2596 and 2597) Furia (CRC handbook of food additives 1972, vol. 1; pp. 644, 645, 647 and 649) 4 pages.*
Furia (CRC handbook of food additives 1972, vol. 1; pp. 644, 645, 647 and 649) 5 pages.*
Ferraz et al. (J. Biomed Mater Res 1999, 45, 376-383).*
Materials Protection, Feb. 1996, vol. 29 No. 2, pp. 10-12., Japan.
Abstract of SU Patent #732218.
Abstract of WO Pub #9310058.
Abstract of RU Patent # 2027778.
Abstract of JP 49-119909.
Abstract of CN Patent #1401612.
Abstract: Zhang, Ling et al.; School of Materials Science and Engineering, Anshan Inst. of I. & S. Technology, 11402, (2000), 23(4), pp. 254-256.
English translation of Office Action dated Nov. 4, 2010 for corresponding Japanese Application No. P2004-204195.
Database WPI, XP 002299261.
Patent Abstracts of Japan, Bd. 200, Nr. 10.

* cited by examiner

*Primary Examiner* — Ernst V Arnold
(74) *Attorney, Agent, or Firm* — Ohlandt, Greeley, Ruggiero & Perie, LLP

(57) ABSTRACT

Described are the use of glass compositions, for example, in the form of glass powders, glass ceramics, fibers, granules, and spheres for achieving an antioxidative effect. The glass compositions may be used in a versatile manner, such as in cosmetic products, medical products, edibles, paints and lacquers, plasters, cements and concrete, in antifouling products and in polymers. Because of the high photo and temperature stability, the glass antioxidants of the present invention are superior to the organic substances known so far. In addition the glass compositions in contact with human being are non-irritant to skin and even edible. Furthermore, they are toxicologically harmless and environmentally compatible.

15 Claims, 2 Drawing Sheets

USE OF GLASS COMPOSITIONS FOR ACHIEVING AN ANTIOXIDATIVE EFFECT

CROSS REFERENCE TO RELATED APPLICATIONS

This application claims the benefit of German Application No. 10332011.3 filed Jul. 14, 2003, which is incorporated by reference herein.

FIELD OF THE INVENTION

The invention relates to the use of glass compositions in the form of glass powders, fibers, granules, and spheres for achieving an antioxidative effect.

The glass compositions according to the present invention may also be transformed into glass ceramics having a different degree of crystallinity by an annealing step and can be used as antioxidants. Also a complete transformation into a ceramic may be carried out.

With it, the glass composition may be used in a versatile manner, such as in cosmetic products (i.a. "anti-aging" products), medical products, edibles and animal food, paints and lacquers, and in polymers.

In this case on the one hand, the employment of the materials described herein may occur for protecting the product itself, but on the other hand also for achieving an antioxidative effect towards outside (e.g. in food additives).

BACKGROUND OF THE INVENTION

While the use of antimicrobially and/or biocidally acting glasses is known from a plurality of documents, the employment of glass compositions to stop or retard an oxidation reaction has completely been unknown so far.

By the use of antioxidants; oxidation reactions which have a negative effect on various products may be stopped retarded; or respectively.

Thus, for example, the presence of free radicals in the above mentioned products may result in undesired decomposition, discoloration or even in the complete uselessness of the product.

Thus the antioxidants may also have product preservative or even product maintaining properties.

Oxidation effects i.a. are also responsible for the aging of the skin. These oxidations, respectively the formation of radicals are caused i.a. by UV radiation of the sun light also by pollutants in the air, and respectively. These effects are i.a. also responsible for the formation of wrinkles. Items antioxidants are also utilized in cosmetic products which should take precautions against a premature aging of the skin (so-called anti wrinkle agents).

The antioxidants described and known so far are almost exclusively organic compounds. Vitamin C (ascorbic acid) and also vitamin E inter alia are well known to a person skilled in the art. Partly these compounds have the disadvantage not to be photo resistant by itself, i.e. that they may act as a free-radical generator. The known oxidant vitamin C i.a. suffers from this disadvantage, in particular when applied in small concentrations.

Thus there is a need for providing an antioxidant which may be used for the above mentioned applications and which doesn't suffer from the disadvantages of the known antioxidants.

SUMMARY OF THE INVENTION

It was surprisingly now found that glass compositions as defined in the claims may be used for the purpose of avoiding oxidation reactions, i.e. as antioxidant. The glass compositions may be oxidic.

The antioxidative compositions of the present invention have a high photo and temperature stability. Preferably the antioxidative glass compositions have a biocidal effect on bacteria, fungi and viruses or they are biostatic. Further preferably in contact with humans they are non-irritant to skin and even edible, in addition toxicologically harmless and environmentally compatible. Thus the compositions are preferably free of heavy metals, in particular when they are in direct contact with living beings.

The glass compositions used in this case comprise glass ceramics, fibers, granules, spheres and glass powders. A glass powder may be a powder that contains a plurality of glass particles in any form (also fibers), for example glass spheres having a particle size (d50) of smaller than 1 mm up to smaller than 500 µm, more preferably <100 µm and <20 ppm, in particular <10 µm and <5 µm, or glass fibers having a diameter of smaller than 1 mm up to smaller than 500 µm, more preferably <100 µm and <20 µm, in particular <10 µm and <5 µm.

Glass ceramics according to the present invention may be prepared by annealing and may have different degrees of crystallinity.

The antioxidative effect may be based on a reaction of the glass with surrounding substances.

Reactions on the glass surface may also contribute to the antioxidative effect. Presumably the compositions produce the antioxidative effect in different manners, for example by the interception of free radicals, but also by the discontinuation of reaction chains which are responsible for the formation of free radicals and/or oxidation reactions and/or the exertion of an effect of chelation.

DETAILED DESCRIPTION OF CERTAIN EMBODIMENTS OF THE INVENTION

According to the following embodiment examples which serve for illustration the invention will be described in more detail:

EXAMPLE 1

Glasses were smelted from the raw materials shown in table 1 which afterwards were formed into ribbons.

By means of dry milling these ribbons were further processed into powder having a particle size of d50=4 µm.

TABLE 1

Compositions (Synthesis Values) [in Percent by Weight] of the Glass Compositions according to the Present Invention

|  | Emb. 1 | Emb. 2 | Emb. 3 |
|---|---|---|---|
| $SiO_2$ | 71.2 | 45 |  |
| $Al_2O_3$ | 0.35 |  | 6.2 |
| $B_2O_3$ |  |  |  |
| $P_2O_5$ |  | 6 | 66.3 |
| $Li_2O$ |  |  |  |
| $Na_2O$ | 14.2 | 24.5 | 12.5 |
| $K_2O$ | 0.05 |  |  |
| $MgO$ | 4.2 |  |  |
| $CaO$ | 9.9 | 24.5 | 7.5 |
| $ZnO$ |  |  | 7.5 |
| $Fe_2O_3$ | 0.1 |  |  |

|  | Emb. 4 | Emb. 5 | Emb. 6 | Emb. 7 | Emb. 8 | Emb. 9 | Emb. 10 | Emb. 11 | Emb. 12 | Emb. 13 | Emb. 14 | Emb. 15 |
|---|---|---|---|---|---|---|---|---|---|---|---|---|
| $SiO_2$ |  |  |  | 44.00 | 44.90 |  | 63.55 | 63.40 | 63.40 | — | — |  |
| $Li_2O$ |  |  |  |  |  |  |  |  |  |  |  |  |
| $Na_2O$ | 11.90 | 11.90 | 14.60 | 24.50 | 24.50 | 14.60 | 6.57 | 6.70 | 5.80 | — | — | 12.50 |
| $K_2O$ |  |  |  |  |  |  |  |  |  | — | — |  |
| $CaO$ |  |  | 3.30 | 24.50 | 24.50 | 3.30 |  |  |  | 11.90 | 11.90 | 7.50 |
| $P_2O_5$ | 66.90 | 65.90 | 33.45 | 6.00 | 6.00 | 33.45 |  |  |  | 65.90 | 65.90 | 66.20 |
| $B_2O_3$ |  |  |  |  |  |  | 29.87 | 29.80 | 29.80 |  |  |  |
| $Al_2O_3$ | 6.20 | 6.20 |  |  |  |  |  |  |  | 6.20 | 6.20 | 6.20 |
| $SO_3$ |  |  | 15.08 |  |  | 15.08 |  |  |  |  |  |  |
| $Ag_2O$ |  | 1.00 |  | 1.00 | 0.10 | 1.00 |  | 0.10 | 1.00 |  | 1.00 | 0.10 |
| $TiO_2$ |  |  |  |  |  |  |  |  |  |  |  |  |
| $ZnO$ | 15.00 | 15.00 | 33.56 |  |  | 32.56 |  |  |  | 16.00 | 15.00 | 7.50 |

The antioxidative efficiency has been detected by means of the so-called "Deoxyribose-Test"

("The Deoxyribose Method", Analytical Biochemistry, 165, 215-219, 1987).

Figure 1:
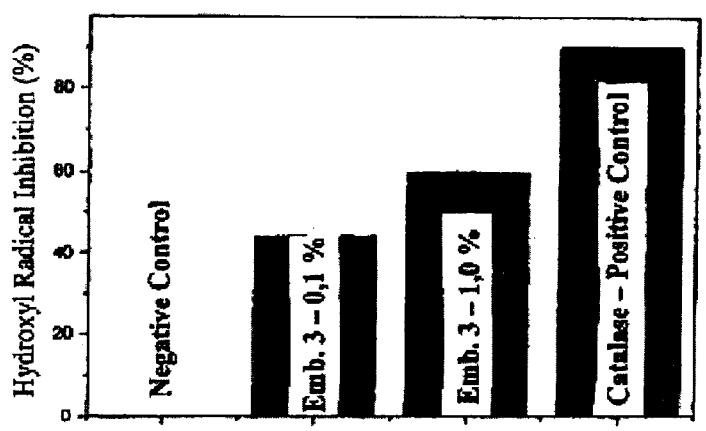
FIG. 1 shows the hydroxyl radical inhibiting effect of embodiment 3 in dependence on the concentration.

The diagram of FIG. 1. shows the hydroxyl radical inhibiting effect of embodiment 3 in dependence on the concentration.

FIG. 1 shows that embodiment 3 produces a clear hydroxyl radical inhibiting effect which increases with rising concentration.

It is possible to show that the antioxidative effect may be based on a discontinuation of the redox reaction chain. In the test method described herein the effect is based on a chelate formation (complexation) of iron which is required for the formation reaction of the free radicals. Thus the $Fe^{(2+)}/Fe^{(3+)}$ redox reaction will be discontinued.

EXAMPLE 2

An alternative test method for detecting the antioxidative effect may be carried out by means of the so-called "Protein-Carbonyl-Assay-Test" which is described in "R. L. Levine et al., Meth. Enzymol. 186, 464-478, 1990".

Figure 2:
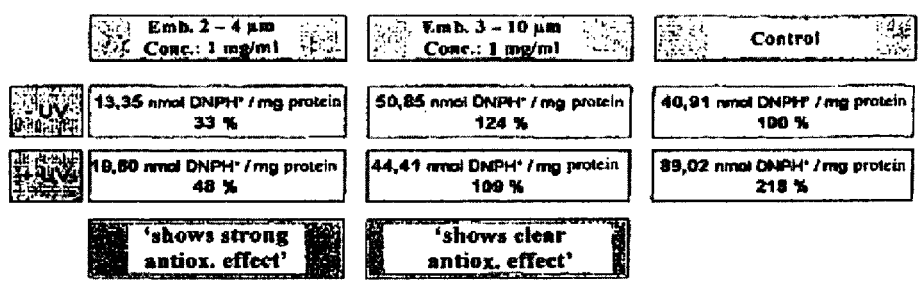
FIGS. 2-3 show the measure of the antioxidative effect on the basis of obtained and oxidized proteins.
Figure 3:
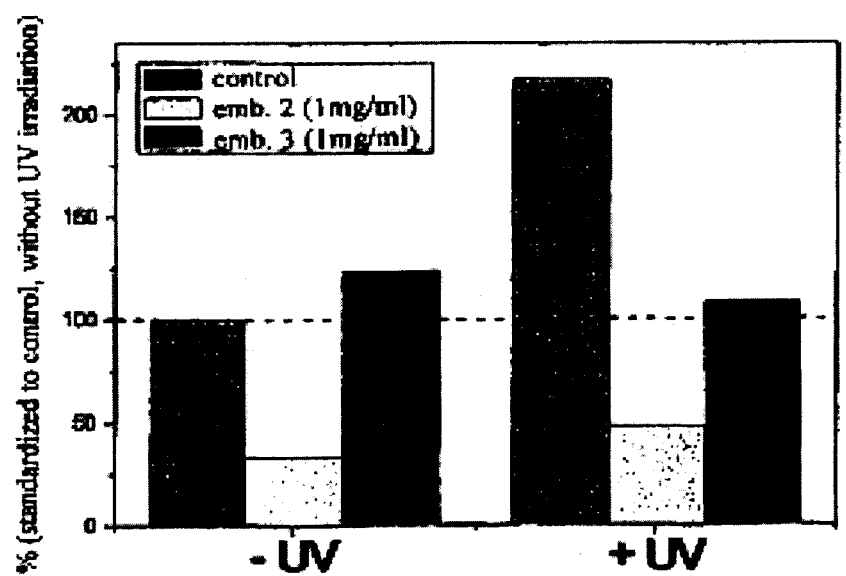

FIGS. 2 and 3 show the measure of the antioxidative effect on the basis of obtained and oxidized proteins. The test was carried out, before the irradiation with UV light (−UV) and after the action of UV light (+UV).

The lower the bar in FIG. 3, the higher the antioxidative effect for the composition in each case.

The bar diagram of FIG. 3 shows that with embodiment 2 only few oxidized proteins were obtained, i.e. that the antioxidative effect was high.

Embodiment 3 also shows a clear antioxidative effect after UV irradiation.

EXAMPLE 3

Deoxyribose-Test for the Determination of the Antioxidative Effect of Shampoos which contain Glass Compositions according to the Present Invention.

TABLE 2

Measured Optical Densities and Inhibition calculated thereof

| Sample/ Concentration | Optical Density at 352 nm, 1% of the Shampoo | % Inhibition | Optical Density at 352 nm, 10% of the Shampoo | % Inhibition |
|---|---|---|---|---|
| Shampoo 1 with 5% glass composition (emb. 2) | 0.3505 | Not determinable | 0.2922 | 15.5 |
| Shampoo 2 with 5% glass composition (emb. 3) | 0.2426 | 29.9 | 0.2477 | 28.4 |

TABLE 2-continued

Measured Optical Densities and Inhibition calculated thereof

| Sample/Concentration | Optical Density at 352 nm, 1% of the Shampoo | % Inhibition | Optical Density at 352 nm, 10% of the Shampoo | % Inhibition |
|---|---|---|---|---|
| Shampoo 3 no glass composition (support) | 0.3808 | Not determinable | 0.3166 | 8.5 |
| Catalase (positive control) | 0.0471 | 86.4 | Not applicable | Not applicable |
| Reference (negative control) | 0.3459 | Not applicable | Not applicable | Not applicable |

From the above table it will be appreciated that the shampoo which contains the glass composition according to embodiment 2 shows a light antioxidative effect when the test concentration of the tested shampoo is 10%.

In the test performed for the shampoo which contains the glass composition according to embodiment 3 a degradation of deoxyribose through hydroxyl radicals in an amount of about 30% can be determined, which corresponds to a distinct antioxidative effect.

The support itself (shampoo 3, without glass composition) shows with an inhibition of 8.5% a light antioxidative effect.

The shampoos 1 to 3 have the following composition (table 3):

| No. | Raw Material | INCI* | Shampoo 1 [percent by weight] | Shampoo 3 [percent by weight] | Shampoo 2 (Support) [percent by weight] |
|---|---|---|---|---|---|
| 1 | Texapon NSO | Sodium laureth sulphate | 50.00 | 50.00 | 50.00 |
| 2 | Amphotensid B4 | Cocamidopropyl betain | 8.0 | 8.0 | 8.0 |
| 3 | Water, demineralized | Water | 33.29 | 38.29 | 33.29 |
| 4 | Euxyl K40() | Methyldibromo-glutaronitril and phenoxyethanol | 0.1 | 0.1 | 0.1 |
| 5 | Edeta BD | Disodium EDTA | 0.1 | 0.1 | 0.1 |
| 6 | Veegum Ultra | Magnesium aluminium silicate | 2.0 | 2.0 | 2.0 |
| 7 | Propylene carbonate | Propylene carbonate | 0.01 | 0.01 | 0.01 |
| 8 | Glass composition according to emb. 2 | | 5.0 | — | — |
| 9 | Glass composition according to emb. 3 | | — | — | 5.0 |
| 10 | NaCl | Sodium chloride | 1.5 | 1.5 | 1.5 |
| | | | 100.00 | 100.00 | 100.00 |
| | pH value | | 10.2 | 5.7 | 5.1 |

*international nomenclature of cosmetic ingredients

EXAMPLE 4

Deoxyribose-Test for the Determination of the Antioxidative Effect of OW Formulations, which contain Glass Compositions according to the Present Invention.

TABLE 4

Measured Optical Densities and Inhibition calculated thereof

| Sample/Concentration | Optical Density at 352 nm, 1% of the OW Formulation | % Inhibition | Optical Density at 352 nm, 10% of the OW Formulation | % Inhibition |
|---|---|---|---|---|
| OW formulation 1 with glass composition (emb. 2) | 0.3986 | Not determinable | 0.3798 | 4.1 |

TABLE 4-continued

Measured Optical Densities and Inhibition calculated thereof

| Sample/ Concentration | Optical Density at 352 nm, 1% of the OW Formulation | % Inhibition | Optical Density at 352 nm, 10% of the OW Formulation | % Inhibition |
|---|---|---|---|---|
| OW formulation 2 with glass composition (emb. 3) | 0.2505 | 36.8 | 0.2039 | 48.5 |
| Catalase (positive control) | 0.0829 | 79.1 | Not applicable | Not applicable |
| Reference (negative control) | 0.3962 | Not applicable | Not applicable | Not applicable |

From the above table it will be appreciated that the OW formulation which contains the glass composition according to embodiment 2 shows a light antioxidative effect if the test concentration of the tested formulation is 10%.

In the test performed for the OW formulation which contains the glass composition according to embodiment 3 a degradation of deoxyribose through hydroxyl radicals in amounts of about 37% respectively 49% can be determined, which correspond to a distinct antioxidative effect.

The OW formulations 1 and 2 have the following compositions (table 5):

| No. | Raw Material | OW Formulation 1 [percent by weight] | OW Formulation 2 [percent by weight] |
|---|---|---|---|
| 1 | Alacel 165 V | 6.65 | 6.65 |
| 2 | Cetyl alcohol (Lanette 16) | 0.95 | 0.95 |
| 3 | Stearingsaure L2 SM (GV S052) | 4.75 | 4.75 |
| 4 | Neutral oil vegetab./ Crodamol GTCC (GV N020) | 22.8 | 22.8 |
| 5 | Demineralized water | 59.85 | 59.85 |
| 6 | Glass composition according to emb. 2 | 5.0 | — |
| 7 | Glass composition according to emb. 3 | — | 5.0 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions

What is claimed is:

1. A method for achieving an antioxidative effect in a cosmetic product or deodorizing product for application to the hair or skin, which comprises adding to the product a glass composition which achieves an antioxidative effect in the product,
wherein said glass composition comprises the following ingredients
$SiO_2$ 0-10 percent by weight
$P_2O_5$ 25-75 percent by weight
$SO_3$ 0-30 percent by weight
$B_2O_3$ 0-40 percent by weight
$Al_2O_3$ 0-10 percent by weight
$Li_2O$ 0-15 percent by weight
$Na_2O$ 0-40 percent by weight
$K_2O$ 0-25 percent by weight
CaO 3.3-40 percent by weight
MgO 0-15 percent by weight
SrO 0-15 percent by weight
BaO 0-15 percent by weight
ZnO 0-40 percent by weight
$Ag_2O$ 0-5 percent by weight
I 0-10 percent by weight and
$Fe_2O_3$ 0-5 percent by weight; and
wherein the glass composition is in the form of fibers, granules, spheres or powders.

2. The method according to claim 1, wherein said glass composition is oxidic.

3. The method according to claim 1, wherein said glass composition has a high photo and temperature stability.

4. The method according to claim 1, wherein in said glass composition the sum of CaO+MgO+SrO+BaO+ZnO is 3.3 to 40 percent by weight.

5. The method according to claim 1, wherein said glass composition is free of alkali.

6. The method according to claim 1, wherein in said glass composition the sum of $Li_2O+Na_2O+K_2O$ is 5 to 50 percent by weight.

7. The method according to claim 1 wherein the glass composition is provided in a cosmetic product.

8. The method according to claim 1 wherein the glass composition is provided in a deodorizing product.

9. The method according to claim 1, wherein the glass composition is provided in a cosmetic product for lessening premature aging of the skin.

10. The method of claim 1, wherein the glass composition is provided in the form of a glass ceramic.

11. The method of claim 1, wherein the glass composition is provided in the form of a glass powder or glass spheres having a particle size, d50, of up to 500 μm or glass fibers having a diameter up to 500 μm.

12. The method of claim 7, wherein the glass composition retards the occurrence of oxidation reactions on the hair or skin to which it is applied.

13. The method of claim 1, wherein the glass composition has 0% by weight of $Ag_2O$.

14. The method of claim 1, wherein the glass composition has 0% by weight of ZnO.

15. A method for achieving an antioxidative effect in a cosmetic product or deodorizing product for application to the hair or skin, which comprises adding to the product a glass-ceramic composition or a ceramic composition which achieves an antioxidative effect in the product,
wherein said glass-ceramic composition or ceramic composition comprises the following ingredients
$SiO_2$ 0-10 percent by weight
$P_2O_5$ 25-75 percent by weight
$SO_3$ 0-30 percent by weight
$B_2O_3$ 0-40 percent by weight
$Al_2O_3$ 0-10 percent by weight
$Li_2O$ 0-15 percent by weight
$Na_2O$ 0-40 percent by weight
$K_2O$ 0-25 percent by weight
CaO 3.3-40 percent by weight
MgO 0-15 percent by weight
SrO 0-15 percent by weight
BaO 0-15 percent by weight
ZnO 0-40 percent by weight
$Ag_2O$ 0-5 percent by weight
I 0-10 percent by weight and
$Fe_2O_3$ 0-5 percent by weight; and
wherein the glass-ceramic composition or ceramic composition is in the form of fibers, granules, spheres or powders.

* * * * *